United States Patent
Nakagawa

(10) Patent No.: US 9,451,907 B2
(45) Date of Patent: Sep. 27, 2016

(54) MEASURING APPARATUS

(75) Inventor: Takashi Nakagawa, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 717 days.

(21) Appl. No.: 13/531,123

(22) Filed: Jun. 22, 2012

(65) Prior Publication Data

US 2012/0330617 A1  Dec. 27, 2012

Related U.S. Application Data

(60) Provisional application No. 61/500,084, filed on Jun. 22, 2011.

(51) Int. Cl.
*G01N 33/487* (2006.01)
*A61B 5/145* (2006.01)
*A61B 5/00* (2006.01)

(52) U.S. Cl.
CPC ..... *A61B 5/14532* (2013.01); *G01N 33/48792* (2013.01); *A61B 5/743* (2013.01); *A61B 2562/0295* (2013.01)

(58) Field of Classification Search
CPC .............. G01N 33/48792; A61B 5/14532; A61B 5/743; A61B 2562/0295; G06F 17/00
USPC ........................................................ 702/187
See application file for complete search history.

(56) References Cited

U.S. PATENT DOCUMENTS

| | | | |
|---|---|---|---|
| 7,241,265 B2 | 7/2007 | Cummings et al. | |
| 7,447,643 B1 * | 11/2008 | Olson et al. | 705/2 |
| 8,626,453 B2 | 1/2014 | Myoujou et al. | |
| 2004/0015102 A1 | 1/2004 | Cummings et al. | |
| 2007/0255123 A1 | 11/2007 | Cummings et al. | |
| 2008/0235053 A1 | 9/2008 | Ray et al. | |

(Continued)

FOREIGN PATENT DOCUMENTS

| | | |
|---|---|---|
| JP | 2004-154547 A | 6/2004 |
| JP | 2010-042261 A | 2/2010 |

(Continued)

OTHER PUBLICATIONS

The extended European Search Report dated Nov. 28, 2012 which corresponds to European Patent Application No./Patent No. 12172246.6-2319/2537467 and is related to U.S. Appl. No. 13/531,123.

(Continued)

*Primary Examiner* — Bryan Bui
(74) *Attorney, Agent, or Firm* — Studebaker & Brackett PC

(57) ABSTRACT

In a measurement situation information storage unit, a plurality of sets of measurement situation information for identifying a measurement situation in which predetermined measurement is performed on a measurement target are stored in association with time periods. A measurement processing unit executes measurement on the measurement target. A display unit selects, from among the plurality of sets of measurement situation information, a set of measurement situation information corresponding to the measurement operation timing based on the time of the measurement operation timing or based on processing results obtained as a result of execution of measurement by the measurement processing unit, and causes a display to show the selected set of measurement situation information in a manner distinguishable from other measurement situation information.

9 Claims, 12 Drawing Sheets

(56) References Cited

U.S. PATENT DOCUMENTS

| | | |
|---|---|---|
| 2009/0247838 A1 | 10/2009 | Cummings et al. |
| 2009/0253973 A1 | 10/2009 | Bashan et al. |
| 2010/0021948 A1 | 1/2010 | Lipman et al. |
| 2010/0160757 A1* | 6/2010 | Weinert et al. ............... 600/365 |
| 2011/0071365 A1* | 3/2011 | Lee et al. ...................... 600/300 |
| 2011/0148905 A1* | 6/2011 | Simmons ........... A61B 5/14532 345/589 |
| 2011/0196217 A1 | 8/2011 | Myoujou et al. |
| 2011/0196515 A1* | 8/2011 | Niki ........................ G01D 7/00 700/83 |
| 2011/0257496 A1* | 10/2011 | Terashima et al. ........... 600/347 |
| 2012/0165640 A1* | 6/2012 | Galley et al. ................. 600/365 |
| 2012/0286953 A1* | 11/2012 | Bousamra et al. ........... 340/540 |

FOREIGN PATENT DOCUMENTS

| | | |
|---|---|---|
| JP | 2010-082009 A | 4/2010 |
| WO | 2011/106029 A1 | 9/2011 |
| WO | 2011/162823 A1 | 12/2011 |

OTHER PUBLICATIONS

An Office Action; "Communication pursuant to Article 94(3) EPC," issued by the European Patent Office on Jul. 24, 2014, which corresponds to European Patent Application No. 12 172 246.6-1660 and is related to U.S. Appl. No. 13/531,123.

An Office Action; "Notice of Reasons for Rejection," issued by the Japanese Patent Office on Oct. 6, 2015, which corresponds to Japanese Patent Application No. 2012-093716 and is related to U.S. Appl. No. 13/531,123.

An Office Action; "Communication pursuant to Article 94(3) EPC," issued by the European Patent Office on Jul. 23, 2015, which corresponds to European Patent Application No. 12 172 246.6-1660 and is related to U.S. Appl. No. 13/531,123.

Communication pursuant to Article 94(3) EPC issued by the European Patent Office on Feb. 24, 2016, which corresponds to European Patent Application No. 12 172 246.6-1660 and is related to U.S. Appl. No. 13/531,123.

* cited by examiner

FIG. 6

Before Breakfast
After Breakfast
Before Lunch
After Lunch
Before Evening Meal
After Evening Meal
Before Bedtime
Unclassified

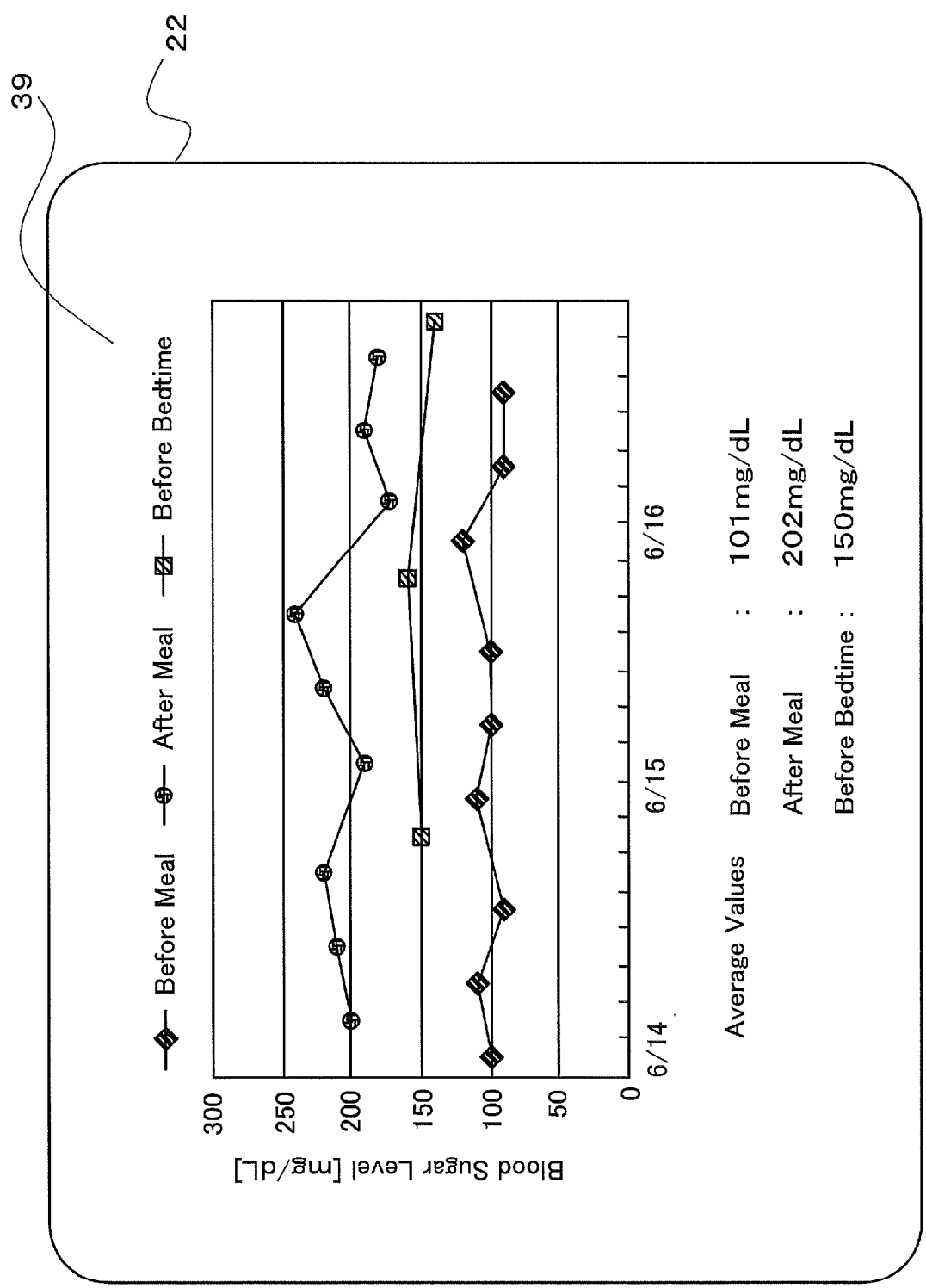

MEASURING APPARATUS

CROSS-REFERENCE TO RELATED APPLICATION

This application claims priority to Japanese Patent Application Nos. 2011-135816 and 2012-93716. The entire disclosure of Japanese Patent Application Nos. 2011-135816 and 2012-93716 is hereby incorporated herein by reference.

BACKGROUND OF THE INVENTION

1. Field of the Invention

The present invention relates to a measuring apparatus capable of identifying a measurement situation in which predetermined measurement is performed on a measurement target.

2. Description of Related Art

In the field of measuring apparatuses for medical use, utilization of measuring apparatuses designed to allow users to easily perform operations has been increasing in recent years. For example, with a small portable blood sugar level meter, when a sensor to which blood as a measurement target has been applied dropwise is inserted into the blood sugar level meter, the value of current, which flows through the blood in proportion to the glucose level of the blood applied dropwise, is measured, and a blood sugar level is calculated from the measured current value. The blood sugar level meter displays the calculated blood sugar level on the display. In this way, small portable blood sugar level meters are configured so as to be capable of easy operation.

The measuring apparatus as described above is desirably configured to display, on the display, the result of computation of predetermined measurement performed on the measurement target, as well as being capable of identifying a measurement situation in which the measurement was made. With such a configuration, it is possible to obtain further detailed information regarding the result of measurement and further enhance the usability of the measuring apparatus.

As an example of such a measuring apparatus, JP 2010-42261A discloses a measuring apparatus configured as a blood sugar level meter that displays a blood sugar level on a display, presents one of a plurality of predetermined flags, and queries the user to select the predetermined flag to associate the flag with the displayed blood sugar level. In response to the query from the measuring apparatus, the user operates a user interface button provided in the measuring apparatus.

JP 2010-42261A also discloses, as the predetermined flags, a before-meal flag, an after-meal flag, and so on. Using such flags enables identification of whether the measurement situation in which measurement was performed is before meal or after meal. With the measuring apparatus disclosed in JP 2010-42261A, however, the user has to repeatedly operate the user interface button as long as the flag presented by the measuring apparatus is different from the flag that is to be associated with the displayed blood sugar level.

SUMMARY OF THE INVENTION

The measuring apparatus disclosed in JP 2010-42261A requires the user to repeatedly perform operations as long as the flag presented by the measuring apparatus is different. This poses problems in that the operation for identifying the measurement situation in which measurement was performed is complicated. The complexity of the operation increases particularly when there are a large number of types of information for identifying the measurement situation in which measurement was performed. It is therefore desirable for measuring apparatuses designed to allow users to easily perform operations to provide ease of performing the operation for identifying the measurement situation in which measurement was performed.

It is an object of the present invention to provide a measuring apparatus that can overcome the above problems and allows the user to easily perform the operation for identifying the measurement situation in which measurement was performed.

Means for Solving the Problem

In order to accomplish the above object, a measuring apparatus according to the present invention includes a measurement situation information storage unit in which a plurality of sets of measurement situation information for identifying a measurement situation in which predetermined measurement is performed on a measurement target are stored in association with time periods; a measurement processing unit that executes measurement on the measurement target; and a display unit that, at a measurement operation timing at which an operation for performing measurement on the measurement target is executed, selects a set of measurement situation information corresponding to the measurement operation timing from among the plurality of sets of measurement situation information stored in the measurement situation information storage unit based on the time of the measurement operation timing or based on processing results obtained as a result of execution of measurement by the measurement processing unit, and causes a display to display the selected set of measurement situation information in a manner distinguishable from other measurement situation information.

With the above features, in the measuring apparatus of the present invention, based on the time of a measurement operation timing or based on results of processing by the measurement processing unit, a set of measurement situation information corresponding to that measurement operation timing is selected from among a plurality of sets of measurement situation information defined in association with time periods, and displayed in a manner distinguishable from other measurement situation information, and therefore can be identified. Therefore, the operation in which the user operates an operation key and selects measurement situation information corresponding to the measurement operation timing can be omitted or eliminated. This eliminates complicated operations that need to be performed repeatedly by the user. Therefore, according to the present invention, the user can easily perform the operation for identifying the measurement situation in which measurement was performed.

It is preferable that the measuring apparatus of the present invention further includes a deciding unit that decides measurement situation information set based on an external input operation or measurement situation information set upon execution of measurement by the measurement processing unit, as the measurement situation information corresponding to the measurement operation timing. With this configuration, the measurement situation information corresponding to the measurement operation timing can be easily decided by an external input operation or execution of measurement.

In the measuring apparatus of the present invention, it is preferable that information for identifying a before-meal measurement situation and information for identifying an after-meal measurement situation are stored in the measurement situation information storage unit as the measurement situation information. With this configuration, the user can easily perform the operation for identifying whether the measurement situation in which measurement was performed is before meal or after meal.

Also, in the measuring apparatus of the present invention, it is preferable that when the before-meal measurement situation information was decided by the deciding unit as the measurement situation information and the measurement operation timing falls in a time period corresponding to the before-meal measurement situation information that had already been decided on the same day, the display unit causes the display to display the after-meal measurement situation information as the measurement situation information. With this configuration, depending on the timing at which before-meal measurement was performed, after-meal measurement situation information can be displayed, and therefore the user's operations can be further simplified flexibly to the user's situation.

Also, in the measuring apparatus of the present invention, it is preferable that information for identifying a before-breakfast measurement situation, information for identifying an after-breakfast measurement situation, information for identifying a before-lunch measurement situation, information for identifying an after-lunch measurement situation, information for identifying a before-evening meal measurement situation, information for identifying an after-evening meal measurement situation, and information for identifying before-bedtime measurement situation are stored in the measurement situation information storage unit as the measurement situation information. With this configuration, the user can easily perform the operation for identifying whether the measurement situation in which measurement was performed is before or after each meal (breakfast, lunch and evening meal) or before bedtime.

Also, the measuring apparatus of the present invention preferably further includes a measurement information storage unit that stores therein information regarding the time of the measurement operation timing and the measurement situation information decided by the deciding unit each time measurement is executed on the measurement target and a frequency determining unit that determines frequencies of time periods to which the times of the measurement operation timing belong for each type of measurement situation information based on the information stored in the measurement information storage unit, and the display unit is preferably capable of changing a selection of measurement situation information based on, in addition to the time of the measurement operation timing, the resulting frequencies determined by the frequency determining unit. With this configuration, the frequencies of time periods of measurement operation timing are determined for each type of measurement situation information based on the past measurement records, and the measurement situation information corresponding to the measurement operation timing is displayed on the display according to the determined result. It is therefore possible to continuously learn patterns of time periods during which the user performs measurement, and further simplify the user's operations flexibly to the trends of time periods.

Also, the measuring apparatus of the present invention preferably further includes a sensor connection portion to which a sensor is connected, and the display unit preferably determines a timing at which the sensor containing a sample as the measurement target was connected to the sensor connection portion as the measurement operation timing. With this configuration, the measuring apparatus configured such that the sample is supplied via the sensor can easily determine the measurement operation timing, at the time of a sensor connecting operation by the user. This eliminates the need for the user to perform an additional operation of causing the measuring apparatus to detect the measurement operation timing, so the user's operations can be further simplified.

Also, in the measuring apparatus of the present invention, it is preferable that the measurement target is blood, and the measurement processing unit performs processing of measuring the blood and calculating a blood sugar level. With this configuration, with the measuring apparatus configured as a blood sugar level meter, the user can easily perform the operation for identifying the measurement situation in which measurement was performed.

Also, the measuring apparatus of the present invention preferably further includes a processing result storage unit that stores therein the measurement situation information decided by the deciding unit and a processing result obtained as a result of execution of measurement by the measurement processing unit and a graph display unit that causes the display to display a time series transitive graph showing the processing results for each type of measurement situation information in a distinguishable manner based on the content stored in the processing result storage unit. With this configuration, the user can easily check the results of processing by the measuring apparatus plotted on a time series transitive graph for each type of measurement situation information in a distinguishable manner on the display of the measuring apparatus. Furthermore, because the transitions of the processing results over time are displayed for each type of measurement situation information in a distinguishable manner, the user can correctly figure out the relationship between the results of processing by the measuring apparatus and the measurement situation in which measurement was performed.

A measuring apparatus according to another aspect of the present invention may be configured such that a measurement mode for executing predetermined measurement on a measurement target is set to either a normal measurement mode or a special measurement mode based on an external operation. The measuring apparatus according to another aspect of the invention further includes: a normal mode processing unit that performs measurement one time when the measurement mode has been set to the normal measurement mode; a special mode processing unit that performs measurement a plurality of times when the measurement mode has been set to the special measurement mode; and an alarm unit that, when the measurement mode has been set to the special measurement mode, generates an alarm to the outside each time one of a plurality of preset alarm times passes after the timing at which the special measurement mode was set.

The measuring apparatus disclosed in JP 2010-42261A is configured to execute predetermined measurement on the measurement target only one time based on a user operation. If a user of the measuring apparatus disclosed in JP 2010-42261A needs to perform measurement again a predetermined time after a given timing at which measurement was performed, the user needs to measure the predetermined time by himself/herself, which causes a possibility that the user might forget to take measurement. In contrast, with a measuring apparatus that has an alarm function of generating an alarm after passage of a preset time set by the user performing a setting operation, the user can be freed from the onerous burden of having to measure time on the user's side.

However, if multiple instances of measurement need to be performed each time one of the preset alarm times passes after a given timing at which measurement was performed, the user needs to repeatedly perform the setting operation for executing the alarm function on the measuring apparatus. This raises the problem in that complicated operations that need to be repeatedly performed occur. Accordingly, a measuring apparatus designed to allow a user to easily perform operations is desirably capable of freeing the user from the onerous burden of having to measure time on the user's side when multiple instances of measurement are necessary and also capable of easy operation.

In the measuring apparatus according to another aspect of the present invention, measurement is executed a plurality of times when the user has set the measurement mode of the measuring apparatus to a special measurement mode, and an alarm is generated to the outside each time one of a plurality of preset alarm times passes after the timing at which the special measurement mode was set. This frees the user from the onerous burden of having to measure time on the user's side. Furthermore, because an alarm is automatically generated each time one of a plurality of preset alarm times passes, the user does not need to repeatedly perform the setting operation for executing the alarm function, so the operations can be simplified. Therefore, according to another aspect of the invention, it is possible to provide a measuring apparatus that can free the user from the onerous burden of having to measure time on the user's side when multiple instances of measurement need to be performed, and also simplify the operations.

Also, in the measuring apparatus according to another aspect of the present invention, it is preferable that a measurement processing unit is further provided that, when a sensor is connected to the sensor connection portion and blood as a measurement target is introduced into the sensor, performs measurement on the blood and calculates the blood sugar level based on an instruction from the normal mode processing unit or the special mode processing unit, and that as the special measurement mode, a postprandial-time-based measurement mode that is set at a timing at which the user eats a meal and a glucose tolerance test measurement mode that is set at a timing at which a predetermined amount of glucose is ingested can be set separately. With this configuration, postprandial-time-based measurement and glucose tolerance test measurement can be set separately as the special measurement mode, so the user can figure out the relationship between the results of processing by the measuring apparatus and the special measurement mode in a more detailed and correct manner.

The above and other objects, as well as features and advantages of the present invention will become apparent from the following description taken in conjunction with the accompanying drawings.

BRIEF DESCRIPTION OF THE DRAWINGS

FIG. 6 is a diagram showing, in the form of a list, measurement situation information stored in a measurement situation information storage unit of the measuring apparatus shown in FIG. 4.

FIG. 8 shows an example of a time series transitive graph screen displayed on the display of the measuring apparatus shown in FIG. 1.

DETAILED DESCRIPTION OF THE INVENTION

Hereinafter, a measuring apparatus according to an embodiment of the present invention will be described with reference to FIGS. 1 to 10.

[Configuration of Measuring Apparatus]

Figure 1:
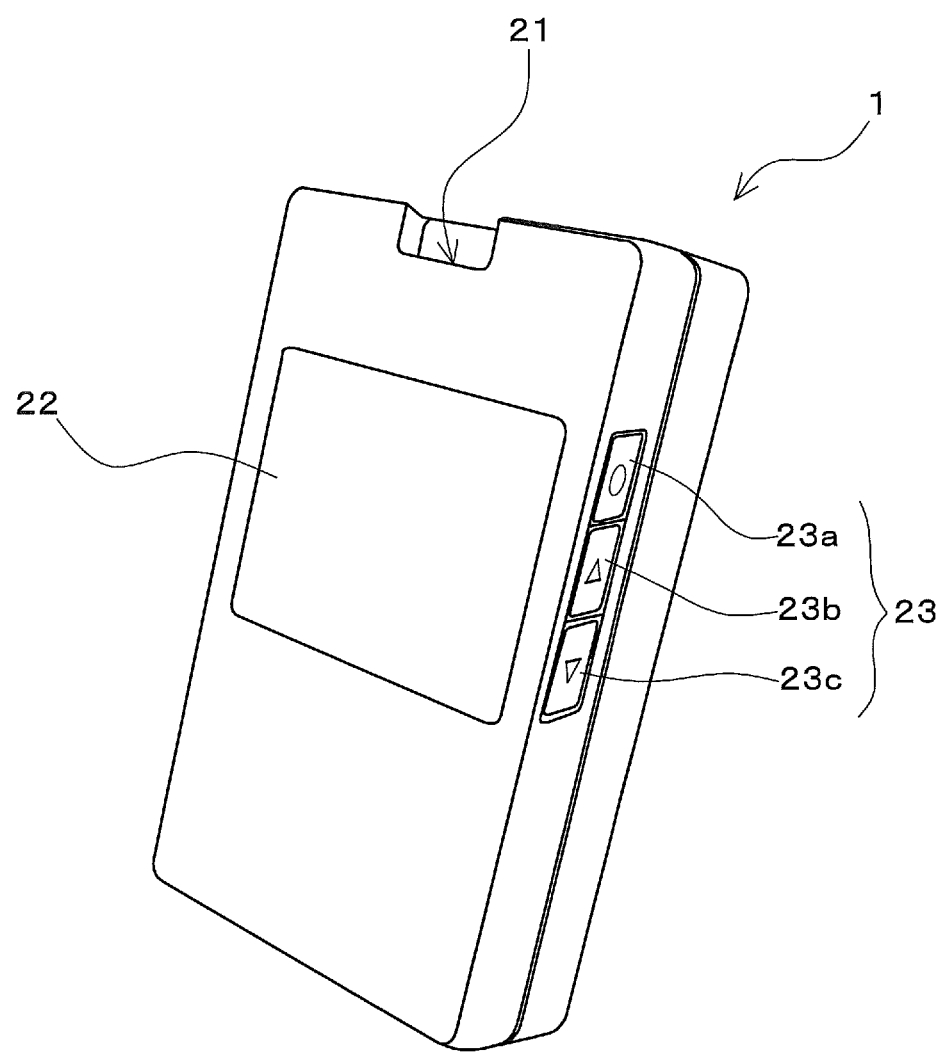
FIG. 1 is a perspective view showing the external appearance of a measuring apparatus according to an embodiment of the present invention.
Figure 2:
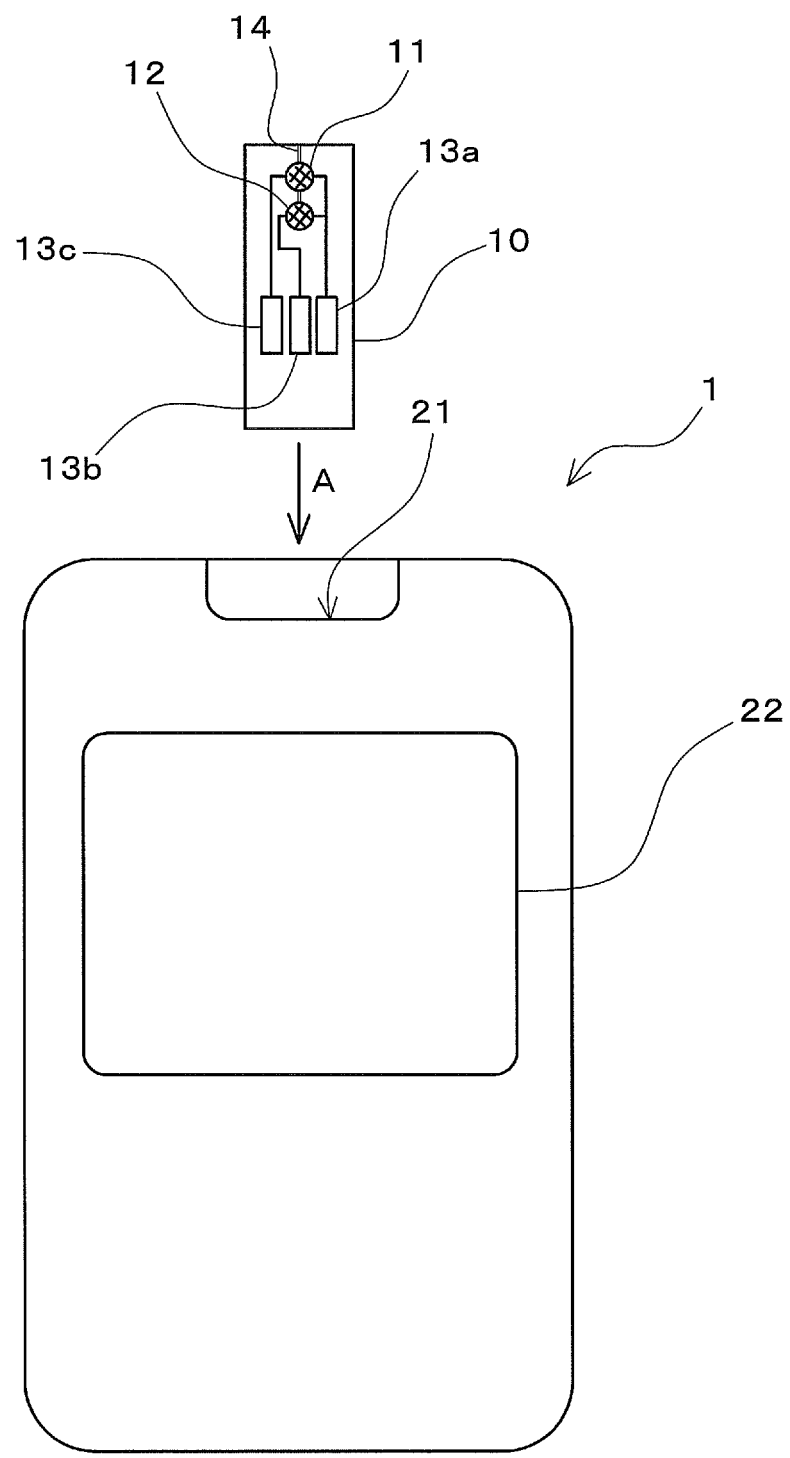
FIG. 2 is a front view showing the external appearance of the measuring apparatus shown in FIG. 1.
Figure 3:
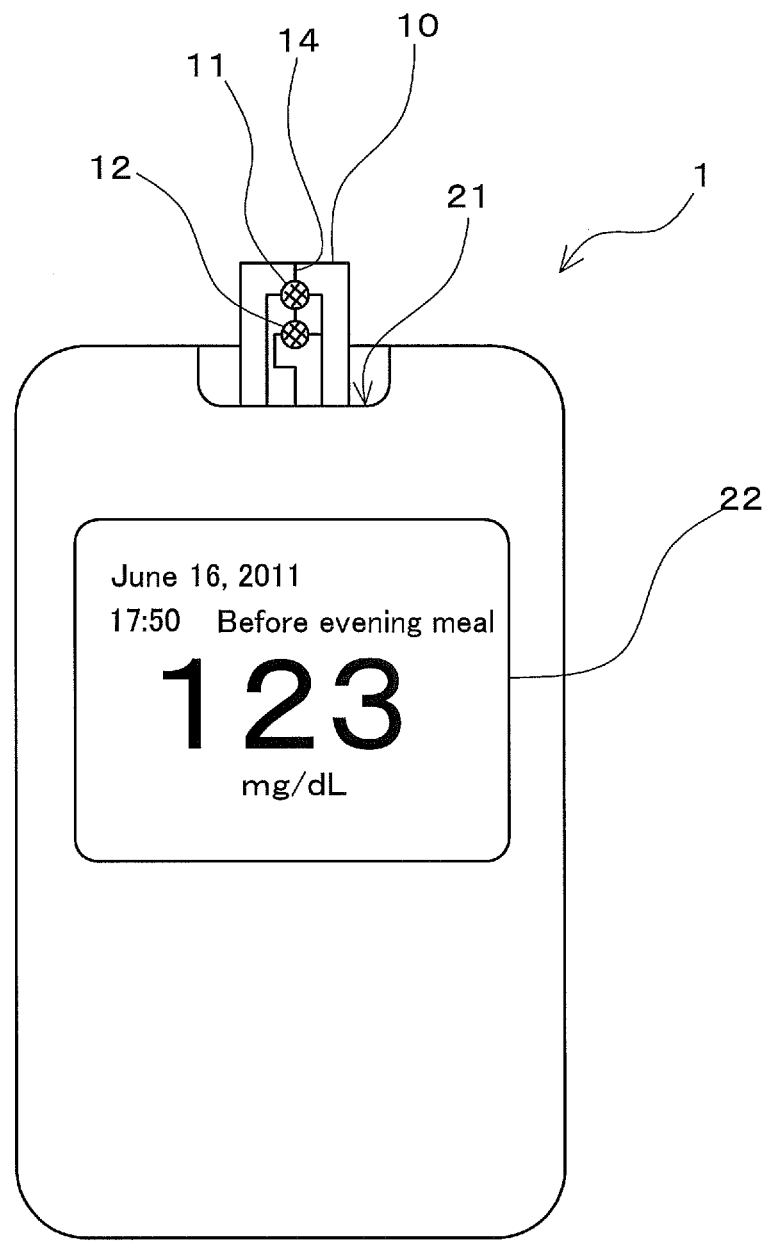
FIG. 3 is a front view showing the external appearance of the measuring apparatus shown in FIG. 1.
Figure 4:
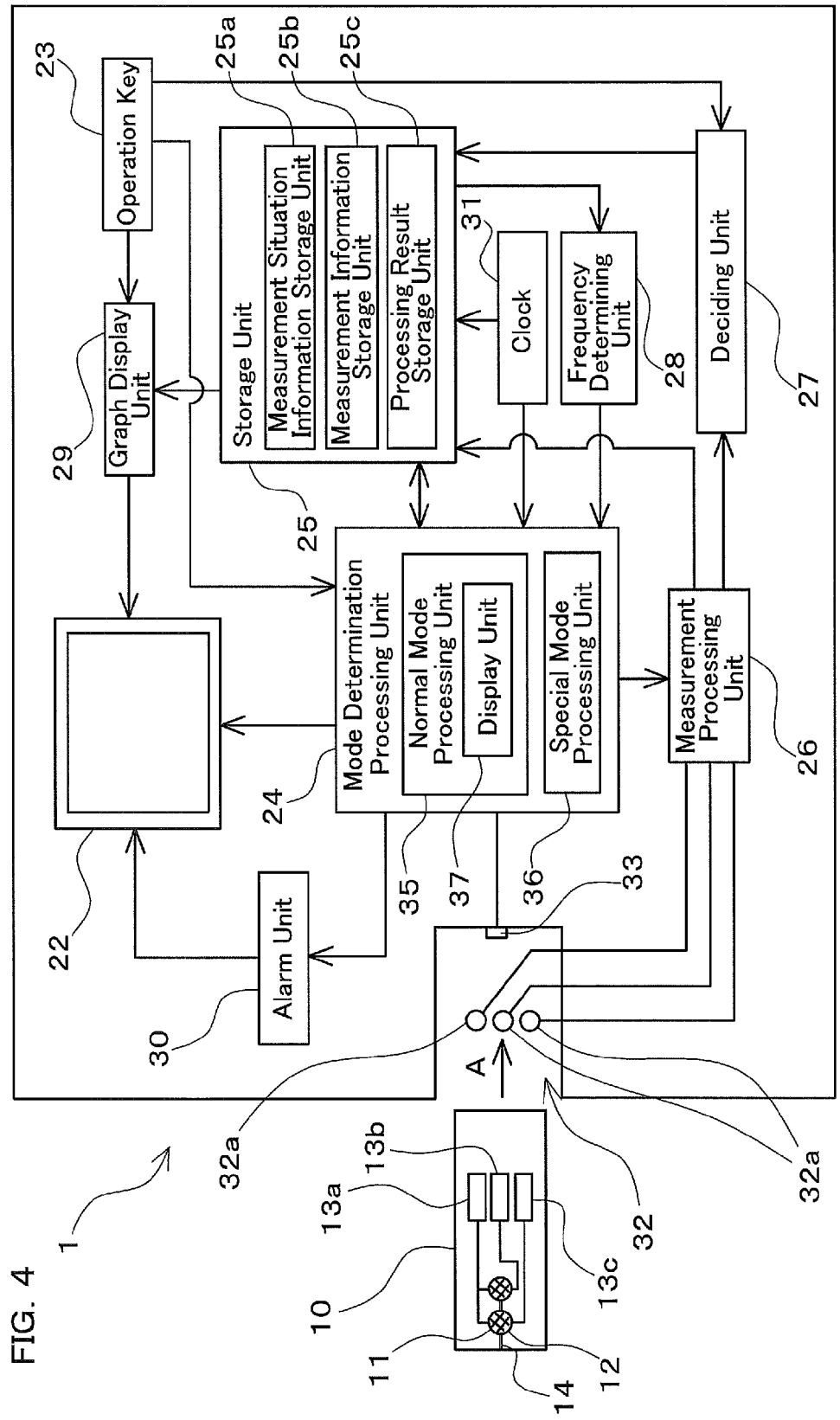
FIG. 4 is a block diagram showing a configuration of the measuring apparatus shown in FIG. 1.

A configuration of a measuring apparatus according to an embodiment of the present invention will be described first with reference to FIGS. 1 to 4. FIG. 1 is an external perspective view of a measuring apparatus 1 according to an embodiment of the present invention. FIGS. 2 and 3 are external front views of the measuring apparatus 1. FIG. 4 is a block diagram showing a configuration of the measuring apparatus 1. The present embodiment will be described taking, as an example, a measuring apparatus 1 configured as a blood sugar level meter that measures the value of current flowing through the blood contained in a connected sensor 10 and calculates a blood sugar level from the measured current value. However, the present invention is not limited to that example, and is applicable to a wide range of applications including measuring apparatuses that perform various types of measurement.

As shown in FIGS. 1 to 3, the measuring apparatus 1 of the present embodiment is provided with an insertion port 21 into which one end in the longitudinal direction of a sensor 10 having a substantially rectangular external shape is inserted along the direction indicated by the arrow A in FIG. 2. The measuring apparatus 1 is further provided with a display 22 and operation keys 23 (23a, 23b, 23c) that are operated by the user.

In the present embodiment, a determination key 23a, an up-scroll key 23b and a down-scroll key 23c are provided as the operation keys 23. The determination key 23a is press-operated by the user so as to enter, for example, an item selected from among menu items displayed on the display 22.

The up-scroll key 23b is press-operated by the user so as to, for example, scroll up through menu items on the scroll menu screen displayed on the display 22, or in other words, to move the displayed position from up to down on the screen. Alternatively, the up-scroll key 23b is press-operated by the user so as to, for example, scroll up a selection position displayed to select one of menu items on the screen, or in other words, to move the displayed selection position from down to up on the screen. In the present embodiment, the term "up" refers to the insertion port 21 side of the screen displayed on the display 22, and "down" refers to the side opposite to the insertion port 21.

The down-scroll key 23c, on the other hand, is press-operated by the user so as to, for example, scroll down through menu items on the scroll menu screen displayed on the display 22, or in other words, to move the displayed position from down to up on the screen. Alternatively, the down-scroll key 23c is press-operated by the user so as to, for example, scroll down a selection position displayed to select one of menu items on the screen, or in other words, to move the displayed selection position from up to down on the screen.

Also, as shown in FIG. 4, the measuring apparatus 1 includes a sensor connection portion 32. The sensor 10 is connected to the measuring apparatus 1 at the sensor connection portion 32 provided in the insertion port 21. The sensor 10 is connected by being inserted into the sensor connection portion 32 along the direction indicated by the arrow A in FIG. 4. In the measuring apparatus 1, in the state in which blood, which is a sample as a measurement target, is supplied to the connected sensor 10, the value of current flowing through the blood in proportion to the blood glucose level is measured, and a blood sugar level is calculated and displayed on the display 22. FIG. 2 shows the measuring apparatus 1 before it is connected to the sensor 10. FIG. 3 shows the measuring apparatus 1 in which a blood sugar level obtained through blood sugar level calculation processing performed after the sensor 10 has been connected is displayed on the display 22.

The configurations of the sensor 10 and the measuring apparatus 1 will now be described in further detail. In the present embodiment, there is no particular limitation on the measurement method of the measuring apparatus 1, and an electrical resistance measurement method or optical measurement method may be used. Note that in the example shown in FIGS. 1 to 4, an electrical resistance measurement method is used, and thus the following description will be given based on the electrical resistance measurement method. In the case where an electrical resistance measurement method is used as the measurement method of the measuring apparatus 1, blood, interstitial fluid and the like can be used as samples as measurement targets. Furthermore, examples of substances to be measured include biological substances of living bodies such as glucose, ketone bodies, cholesterol, lactic acid, uric acid and bilirubin. Other examples include drugs such as sodium fluoride, ascorbic acid and acetaminophen.

In the present embodiment, since the measuring apparatus 1 uses an electrical resistance measurement method, the sensor 10 includes sample measuring portions 11 and 12 and terminals 13a, 13b and 13c for supplying current to each of the sample measuring portions (11, 12). Accordingly, in the measuring apparatus 1, three connection terminals 32a that are respectively connected to the terminals 13a to 13c of the sensor 10 are provided in the sensor connection portion 32 as shown in FIG. 4. To supply a sample to the sensor 10, the sample is applied, for example, dropwise to the end portion of the sensor 10 that is opposite to the end portion that is connected to the sensor connection portion 32 while the sensor 10 is connected to the sensor connection portion 32. The sample applied dropwise is supplied to the sample measuring portions (11, 12) via a guide path 14.

In the present embodiment, as shown in FIG. 4, the measuring apparatus 1 further includes a mode determination processing unit 24, a storage unit 25, a measurement processing unit 26, a deciding unit 27, a frequency determining unit 28, a graph display unit 29, an alarm unit 30, and a clock 31 having a timepiece function of measuring time.

The mode determination processing unit 24 determines a measurement mode that has been set based on an external operation to execute predetermined measurement on the measurement target, and executes processing based on the determined measurement mode. In the present embodiment, the predetermined measurement is measurement that is performed on the sample contained in the sensor 10 so as to calculate the blood sugar level. The mode determination processing unit 24 is constituted by a processor, and for example, the deciding unit 27 and the frequency determining unit 28, which will be described later, are also constituted by identical processors.

In the measuring apparatus 1 of the present embodiment, the measurement mode is set to either a normal measurement mode or a special measurement mode based on a user's external operation performed as operation of connecting the sensor 10 or operation of any of the operation keys 23. Specifically, if the user does not perform a predetermined operation for a predetermined period of time after the sensor 10 has been inserted into and connected to the sensor connection portion 32 by the user, the measurement mode is set to the normal measurement mode.

In this case, upon insertion of the sensor 10 into the sensor connection portion 32, the inserted end portion of the sensor 10 abuts against a limit switch 33 provided in the sensor connection portion 32, and the limit switch 33 is thereby activated. As a result, an activation signal of the limit switch 33 is detected by the mode determination processing unit 24. Then, if it is determined, based on the time measured by the clock 31, that the predetermined period of time has passed, the mode determination processing unit 24 determines that the measurement mode has been set to the normal measurement mode.

Figure 5:
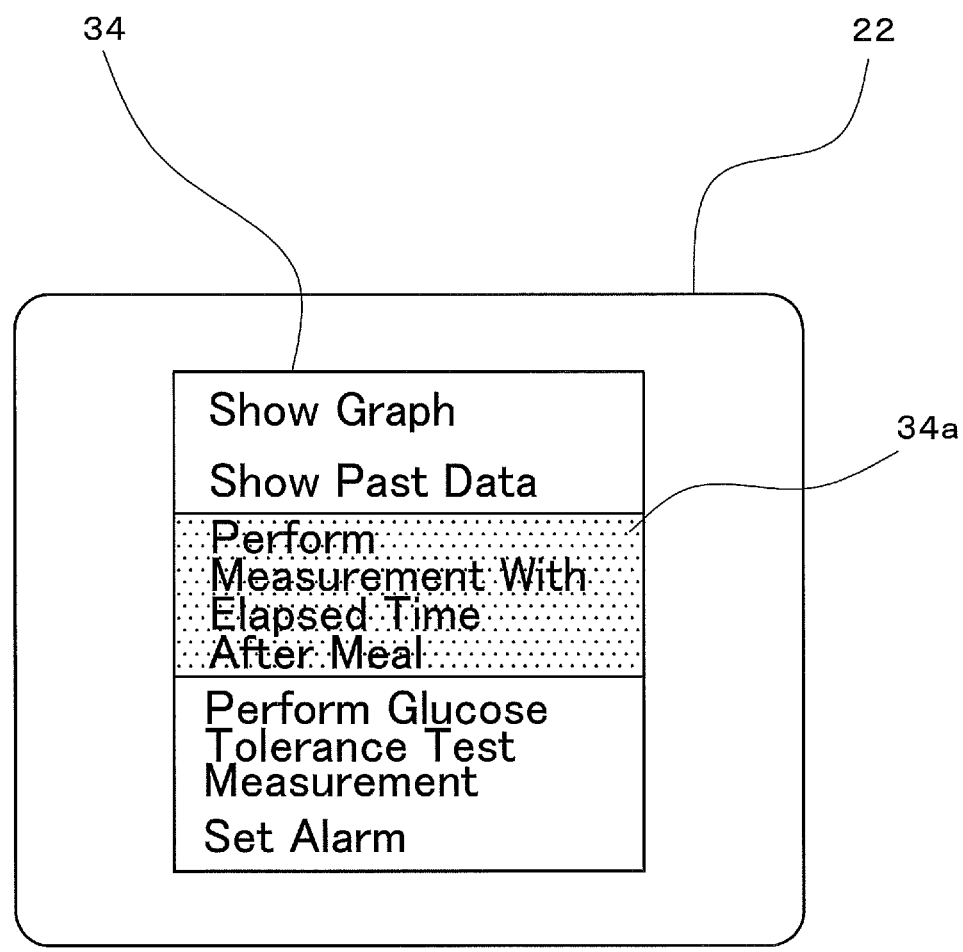
FIG. 5 is a diagram showing an example of a menu screen displayed on a display of the measuring apparatus shown in FIG. 1.

If, on the other hand, the user performs a predetermined operation before the predetermined period of time passes after the start of activation of the limit switch 33, a menu screen 34 as shown in FIG. 5 is displayed on the display 22. The predetermined operation can be, for example, a long press-operation of the determination key 23a of the operation keys 23 (for example, an operation in which the key is kept pressed for several seconds or more), an operation in which the up-scroll key 23b and the down-scroll key 23c are simultaneously pressed, or other operation.

The menu screen 34 displays menu items such as "Show Graph", "Show Past Data", "Measurement With Elapsed Time After Meal", "Glucose Tolerance Test" and "Set Alarm". FIG. 5 shows an example in which "Measurement With Elapsed Time After Meal" has been selected with a selection position 34a displayed to select one of the menu items on the menu screen 34. The user may press-operate the up-scroll key 23b or the down-scroll key 23c when he/she wants to scroll up or down the selection position 34a to select other menu items. Any method can be used as the display method of the selection position 34a, and for example, methods such as changing the background color and highlighting can be used.

In the menu screen 34 shown in FIG. 5, if the user press-operates the determination key 23a while "Measurement With Elapsed Time After Meal" or "Glucose Tolerance Test Measurement" is selected by the selection position 34a, selection of "Measurement With Elapsed Time After Meal" or "Glucose Tolerance Test Measurement" is determined. Upon determination of selection of "Measurement With Elapsed Time After Meal" or "Glucose Tolerance Test Measurement", the mode determination processing unit 24 determines that the measurement mode has been set to a special measurement mode. In this way, the measuring apparatus 1 of the present embodiment is configured such that, as the special measurement mode, the postprandial-time-based measurement mode and the glucose tolerance test measurement mode can be separately set.

The postprandial-time-based measurement mode is configured as the special measurement mode that is set at the timing at which the user eats a meal. If the postprandial-time-based measurement mode is set as the special measurement mode, postprandial-time-based measurement is performed in which measurement is carried out a plurality of times at a specified time interval after the meal.

The glucose tolerance test measurement mode is configured as the special measurement mode that is set at the timing at which the user ingests a predetermined amount of glucose. If the glucose tolerance test measurement mode is set as the special measurement mode, glucose tolerance test measurement is performed in which measurement is carried out a plurality of times at a specified time interval after ingestion of the predetermined amount of glucose. The specified time interval in the postprandial-time-based measurement and the glucose tolerance test measurement is not necessarily set to the same time interval between multiple instances of measurement, and may be set to different time intervals between multiple instances of measurement.

The mode determination processing unit 24 also includes a normal mode processing unit 35 and a special mode processing unit 36. The normal mode processing unit 35 is configured to instruct the measurement processing unit 26, which will be described later, to execute a single instance of measurement when the measurement mode has been set to the normal measurement mode. The special mode processing unit 36 is configured to instruct the measurement processing unit 26, which will be described later, to execute multiple instances of measurement when the measurement mode has been set to the special measurement mode.

If the postprandial-time-based measurement mode is set as the special measurement mode, the special mode processing unit 36 causes the storage unit 25 to store the time when the postprandial-time-based measurement mode was set by the user operating the operation keys 23 as the meal start time. After that, postprandial-time-based measurement in which multiple instances of measurement are carried out is executed by the measurement processing unit 26 based on the instructions from the special mode processing unit 36.

If, on the other hand, the glucose tolerance test measurement mode is set as the special measurement mode, the special mode processing unit 36 causes the storage unit 25 to store the time when the glucose tolerance test measurement mode was set by the user operating the operation keys 23 as the glucose tolerance test start time. After that, glucose tolerance test measurement in which multiple instances of measurement are carried out is executed by the measurement processing unit 26 based on the instructions from the special mode processing unit 36.

In the case of the postprandial-time-based measurement in which multiple instances of measurement are carried out and the glucose tolerance test measurement in which multiple instances of measurement are carried out, the sensor 10 is connected to the sensor connection portion 32 a plurality of times at different timings. A new sensor 10 containing a sample taken from the user at a different timing is used as the sensor 10 that is connected to the sensor connection portion 32 at different timings.

When the measurement mode has been set to either of the special measurement modes, namely, to either the postprandial-time-based measurement mode or the glucose tolerance test measurement mode, the alarm unit 30 generates an alarm to the outside when one of a plurality of preset alarm times passes after the special measurement mode has been set. Specifically, the alarm unit 30 outputs an alarm tone and at the same time causes the display 22 to display an alarm message such as "It's time for measurement".

When the measurement mode has been set to the postprandial-time-based measurement mode, the alarm unit 30 generates an alarm, for example, each time one of preset alarm times (30, 60, 90 and 120 minutes) passes from the time when the postprandial-time-based measurement mode was set. In other words, in this case, the alarm unit 30 generates an alarm at intervals of 30, 60, 90 and 120 minutes after the time when the postprandial-time-based measurement mode was set.

When the measurement mode has been set to the glucose tolerance test measurement mode, the alarm unit 30 generates an alarm, for example, each time one of preset alarm times (1 hour and 2 hours) passes from the time when the glucose tolerance test measurement mode was set. In other words, in this case, the alarm unit 30 generates an alarm at intervals of 1 hour and 2 hours after the time when the glucose tolerance test measurement mode was set.

Each time the alarm is generated, the user is prompted by the alarm and connects the sensor 10 containing a sample to the sensor connection portion 32, and thereby postprandial-time-based measurement or glucose tolerance test measurement is performed.

The storage unit 25 is provided as a memory for storing information required to operate the measuring apparatus 1, information obtained as a result of operation of the measuring apparatus 1, and other information. The storage unit 25 includes a measurement situation information storage unit 25a, a measurement information storage unit 25b and a processing result storage unit 25c. The measurement situation information storage unit 25a, the measurement information storage unit 25b and the processing result storage unit 25c are configured as different storage areas in the memory constituting the storage unit 25.

In the measurement situation information storage unit 25a, a plurality of sets of measurement situation information for identifying the measurement situation in which measurement was performed on the sample contained in the sensor 10, which is started by the sensor 10 being connected to the sensor connection portion 32, are stored in association with a series of time periods during one day. In the measurement situation information storage unit 25a, as the measurement situation information, information for identifying before-meal measurement situations and information for identifying after-meal measurement situations are stored. More specifically, in the measurement situation information storage unit 25a, as the measurement situation information, information for identifying measurement situations, such as "Before Breakfast", "After Breakfast", "Before Lunch", "After Lunch", "Before Evening Meal", "After Evening Meal" and "Before Bedtime", are stored.

FIG. 6 is a diagram showing the measurement situation information stored in the measurement situation information storage unit 25a in the form of a list. As indicated in the order of list shown in FIG. 6, the measurement situation information "Before Breakfast", "After Breakfast", "Before Lunch", "After Lunch", "Before Evening Meal", "After Evening Meal" and "Before Bedtime" are stored in this order in the measurement situation information storage unit 25a, in association with the series of time periods during one day.

In the measurement situation information storage unit 25a, the time periods during one day that correspond to each measurement situation information are also stored. For example, the time period from 5 a.m. to 8 a.m. is stored as "Before Breakfast" time period, the time period from 8 a.m. to 11 a.m. is stored as "After Breakfast" time period, the time period from 11 a.m. to 1 p.m. is stored as "Before Lunch" time period, the time period from 1 p.m. to 5 p.m. is stored as "After Lunch" time period, the time period from 5 p.m. to 8 p.m. is stored as "Before Evening Meal" time period, the time period from 8 p.m. to 10 p.m. is stored as "After Evening Meal" time period, and the time period from 10 p.m. to 2 a.m. is stored as "Before Bedtime" time period.

In the measurement situation information storage unit 25a, as shown in FIG. 6, measurement situation information for identifying "Unclassified" is also stored as measurement situation information other than "Before Breakfast", "After Breakfast", "Before Lunch", "After Lunch", "Before Evening Meal", "After Evening Meal" and "Before Bedtime". The "Unclassified" measurement situation information is used when, for example, measurement is performed when the user is in a poor health condition, or when measurement is performed during the late night period.

Also, the normal mode processing unit 35 includes a display unit 37. At a measurement operation timing at which the operation for performing measurement on the sample contained in the sensor 10 is executed, the display unit 37 selects, from among the plurality of sets of measurement situation information stored in the measurement situation information storage unit 25a, a set of measurement situation information corresponding to the measurement operation timing based on the time of the timing of measurement operation. Then, the display unit 37 further causes the display 22 to display the selected set of measurement situation information in a manner distinguishable from other measurement situation information.

Figure 7A:
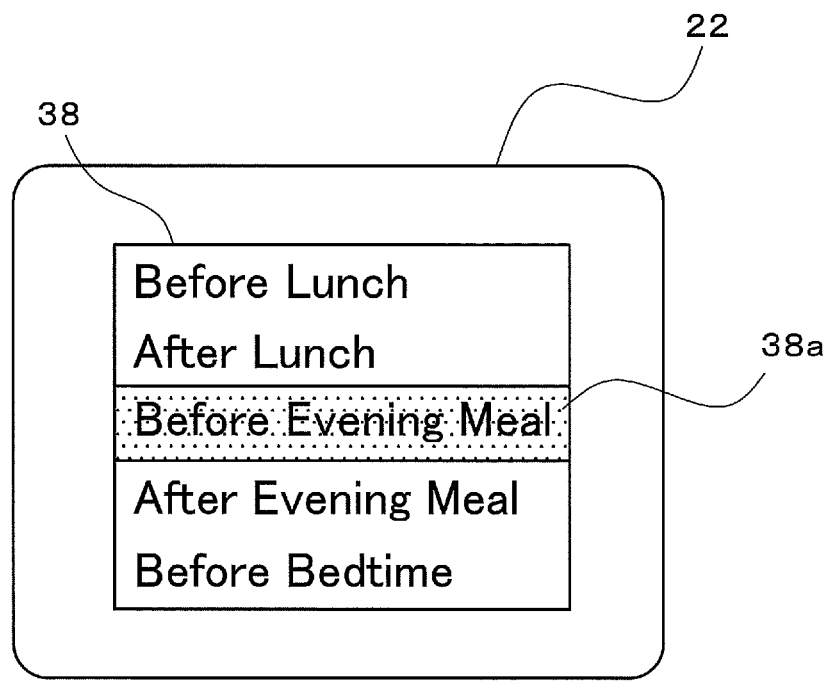
FIG. 7A shows an example of a scroll menu screen displayed on the display of the measuring apparatus shown in FIG. 1.

FIG. 7A is a diagram showing an example of a scroll menu screen 38 displayed on the display 22 by the display unit 37 at a measurement operation timing. The scroll menu screen 38 is displayed as a screen in which menu items corresponding to the measurement situation information are scrolled up and down by user's operations of the up and down scroll keys (23b, 23c). FIG. 7A shows, as an example, the scroll menu screen 38 showing some (5 items in the present embodiment) of all items of the measurement situation information (8 items in the present embodiment). In the scroll menu screen 38, if the up-scroll key 23b is continuously operated, the displayed menu items are routinely scrolled in the order of, for example, "Before Breakfast", "Unclassified", "Before Bedtime", "After Evening Meal", "Before Evening Meal", "After Lunch", "Before Lunch", "After Breakfast" and "Before Breakfast". If, on the other hand, the down-scroll key 23c is continuously operated, the displayed menu items are routinely scrolled in the order of, for example, "Before Breakfast", "After Breakfast", "Before Lunch", "After Lunch", "Before Evening Meal", "After Evening Meal" and "Before Bedtime", "Unclassified" and "Before Breakfast".

The display unit 37 selects, from among the plurality of sets of measurement situation information ("Before Breakfast", "After Breakfast", "Before Lunch", "After Lunch", "Before Evening Meal", "After Evening Meal" and "Before Bedtime"), a set of measurement situation information corresponding to the measurement operation timing based on the time of the timing of measurement operation, which is measured by the clock 31. For example, if the time of the timing of measurement operation is 5:10 p.m., because the time belongs to the time period from 5 p.m. to 8 p.m. defined above as "Before Evening Meal" time period, the display unit 37 selects the measurement situation information "Before Evening Meal" as initial (default) measurement situation information.

Then, the display unit 37 causes the display 22 to display the selected set of measurement situation information "Before Evening Meal" in a manner distinguishable from other measurement situation information. FIG. 7A shows, as an example, the scroll menu screen 38 in which the measurement situation information "Before Evening Meal" has been selected by default. In the scroll menu screen 38 shown in FIG. 7A, a selection position 38a that is shown for the user to select one of the menu items is displayed such that its displayed position is fixed at the center in the vertical direction of the scroll menu screen 38 and the menu items are scrolled up and down. Any method can be used as the method for displaying the initial measurement situation information selected and displayed by the display unit 37 in a manner distinguishable from other measurement situation information. For example, methods such as changing the background color and highlighting can be used.

Also, when, for example, the determination key 23a is press-operated for only a short period of time as is normally the case, rather than being long pressed, after the sensor 10 containing the sample has been connected to the sensor connection portion 32, the display unit 37 determines the timing at which the short press-operation was performed as the measurement operation timing. In this case, the press-operation of the determination key 23a after connection of the sensor 10 to the sensor connection portion 32 corresponds to the operation for performing measurement on the sample contained in the sensor 10.

In the case where the special mode processing unit 36 is not provided in the measuring apparatus 1, the display unit 37 determines a timing at which, for example, the sensor 10 containing the sample is connected to the sensor connection portion 32 as the measurement operation timing. In this case, a timing at which the limit switch 33 is activated by the sensor 10 being connected to the sensor connection portion 32, the sample is applied dropwise to the sensor 10, and the sample measuring portions (11, 12) are energized is determined as the measurement operation timing. Alternatively, a timing at which the limit switch 33 is activated by the sensor 10 to which the sample has been applied dropwise being connected to the sensor connection portion 32 is determined as the measurement operation timing.

The measurement processing unit 26 executes measurement on the sample as the measurement target. Specifically, when the sensor 10 containing blood as the sample has been connected to the sensor connection portion 32, the measurement processing unit 26 measures, based on an instruction from the normal mode processing unit 35 or the special mode processing unit 36, the value of current flowing through the blood and calculates the blood sugar level from the measured current value by using, for example, a calibration curve. In other words, the value of current flowing through the sample measuring portions (11, 12) to which the sample has been supplied is measured and the blood sugar level is calculated.

The sensor 10 may be configured to include a single sample measuring portion only, but from the viewpoint of measurement accuracy, it may be configured to include a plurality of sample measuring portions as in the present embodiment (two sample measuring portions 11 and 12 are included in the present embodiment). The sample introduced into the sensor 10 via the guide path 14 is supplied to each of the sample measuring portions (11, 12). Different reagents can be disposed in the sample measuring portions (11, 12). For example, a reagent that reacts with a substance to be measured is disposed in the sample measuring portion 11, and a reagent that reacts with another substance (biological substance, drug and the like) that coexists with the substance to be measured or a reagent whose response varies according to the properties of the sample (viscosity, salt concentration, hematocrit value and the like) is disposed in the sample measuring portion 12.

In the case of the above configuration, the measurement processing unit 26 can obtain in addition to information regarding the substance to be measured, information (amount and the like) regarding another substance that coexists therewith, and information regarding the properties of the sample. Specifically, if it is assumed that the sample is blood and the substance to be measured is glucose, a reagent that reacts with glucose is disposed in the sample measuring portion 11, and a reagent that exhibits different responses according to the hematocrit value is disposed in the sample measuring portion 12. In this case, the measurement processing unit 26 can obtain information for identifying the glucose concentration and information for identifying the hematocrit value. Then, the measurement processing unit 26 can correct the influence of hematocrit value on the glucose concentration measurement based on the obtained information, so the glucose concentration can be calculated with higher accuracy.

Figure 7B:
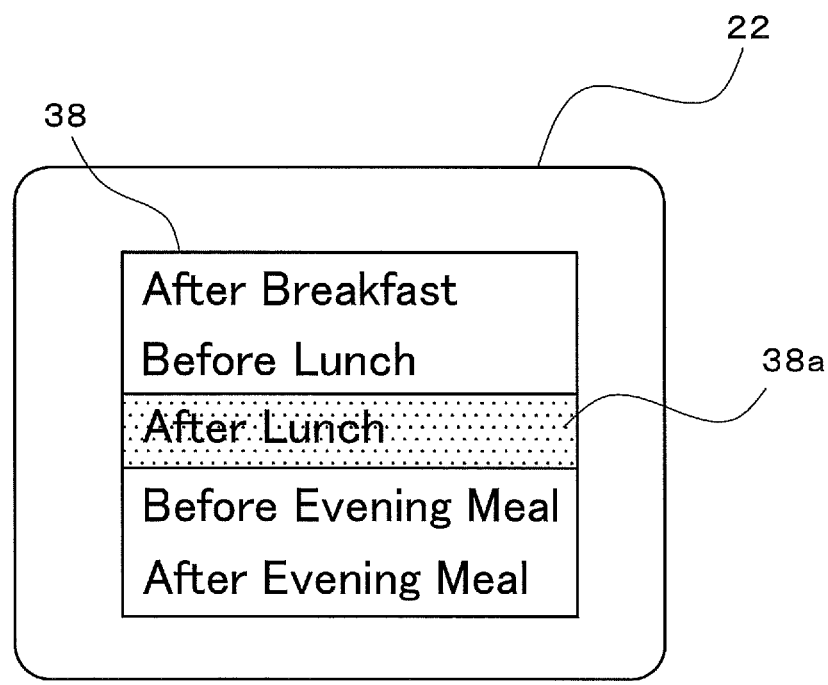
FIG. 7B shows an example of a scroll menu screen displayed on the display of the measuring apparatus shown in FIG. 1.

The deciding unit 27 decides measurement situation information that has been set based on a user's external input operation as measurement situation information that finally corresponds to the aforementioned measurement operation timing. Specifically, if the user determines that the measurement situation information that has been selected by the display unit 37 as the initial measurement situation information and is displayed in a manner distinguishable from other measurement situation information properly corresponds to the measurement operation timing, the user press-operates the determination key 23*a*. Alternatively, if the user determines that the initial measurement situation information displayed does not properly correspond to the measurement operation timing, the user operates the up and down scroll keys (23*b*, 23*c*) so as to scroll the scroll menu screen 38. FIG. 7B shows the scroll menu screen 38 in which "After Lunch" measurement situation information is in the selection position 38*a* as a result of the user operating the up-scroll key 23*b* in the scroll menu screen 38 shown in FIG. 7A. In the state in which the measurement situation information that the user has determined to properly correspond to the measurement operation timing is displayed in the selection position 38*a*, the user press-operates the determination key 23*a*. When a measurement situation information setting operation based on this external input operation has been performed, the measurement situation information deciding unit 27 decides the set measurement situation information as the measurement situation information that finally corresponds to the measurement operation timing.

In the example given above, a configuration was described in which the deciding unit 27 decides the measurement situation information that has been set based on a user's external input operation as the measurement situation information that finally corresponds to the measurement operation timing, but the configuration may be different. The configuration may be such that the deciding unit 27 decides measurement situation information set upon execution of measurement by the measurement processing unit 26, as the measurement situation information that finally corresponds to the measurement operation timing. In this case, for example, the measurement situation information displayed in the selection position 38*a* in the scroll menu screen 38 upon completion of processing by the measurement processing unit 26 is decided as the measurement situation information that finally corresponds to the measurement operation timing, without user's operation of the determination key 23*a* using the scroll menu screen 38.

Also, in the present embodiment, the display unit 37 is configured to, in the case where before-meal measurement situation information was decided as the measurement situation information by the deciding unit 27, and the measurement operation timing is determined to be the time period corresponding to the before-meal measurement situation information that had already been decided on the same day, cause the display 22 to display after-meal measurement situation information as the measurement situation information.

A specific example of the above configuration will be described taking, as an example, the case where "Before Evening Meal" measurement situation information was already decided as the measurement situation information in the previous measurement in which the measurement operation was performed at 6 p.m., and the current measurement is performed at 6:30 p.m. on the same day. In the measurement situation information storage unit 25*a*, the time period from 5 p.m. to 8 p.m. is stored as "Before Evening Meal" time period, and the time period from 8 p.m. to 10 p.m. is stored as "After Evening Meal" time period. Accordingly, in this case, based on the content stored in the measurement situation information storage unit 25*a*, 6:30 p.m., which is the time when the current measurement is performed, is undesirably determined to correspond to the time period of "Before Meal" despite the fact that it is actually after meal.

To address this, in the case where "Before Evening Meal" measurement situation information was already decided by the deciding unit 27 as the measurement situation information in the previous measurement performed at 6 p.m., and the time of the timing of the current measurement operation (6:30 p.m.) falls in the time period (5 p.m. to 8 p.m.) corresponding to the "Before Evening Meal" measurement situation information that had already been decided on the same day, the display unit 37 selects "After Evening Meal" measurement situation information as the measurement situation information corresponding to the current measurement operation timing, and displays the selected information in the selection position 38*a* of the scroll menu screen 38 as the initial measurement situation information.

Also, in the present embodiment, as described above, the storage unit 25 includes the measurement information storage unit 25*b*. The measurement information storage unit 25*b* stores therein information regarding the time of the timing of measurement operation and the measurement situation information decided by the deciding unit 27 each time measurement is executed on the sample. Furthermore, the measuring apparatus 1 of the present embodiment includes the frequency determining unit 28. The frequency determining unit 28 determines the frequencies of time periods to which the times of the timing of measurement operation belong for each type of measurement situation information based on the information stored in the measurement information storage unit 25b. The display unit 37 is configured to be capable of changing a selection of measurement situation information based on, in addition to the time of the timing of measurement operation, the resulting frequencies determined by the frequency determining unit 28. A pattern of time period during which the user performs measurement is thereby learned continuously. The display unit 37 then displays the measurement situation information, to which the results of learning are reflected, in the selection position 38a of the scroll menu screen 38 as the initial measurement situation information.

Also, in the present embodiment, as described above, the storage unit 25 includes the processing result storage unit 25c. The processing result storage unit 25c stores therein the measurement situation information decided by the deciding unit 27 and the processing result obtained by execution of measurement by the measurement processing unit 26. Also, the measuring apparatus 1 of the present embodiment further includes the graph display unit 29. The graph display unit 29 causes the display 22 to display a time series transitive graph showing the processing results for each type of measurement situation information in a distinguishable manner, based on the content stored in the processing result storage unit 25c.

FIG. 8 shows a time series transitive graph screen 39 displayed on the display 22 by the graph display unit 29. As shown in FIG. 8, the graph display unit 29 is configured to, for example, based on the content stored in the processing result storage unit 25c, cause the display 22 to display a time series transitive graph showing the levels of blood sugar as the processing results for respective types of measurement situation information, such as before meal, after meal and before bedtime, in a distinguishable manner. It is preferable that the time series transitive graph screen 39 is output and displayed in color on the display 22 by using a color display device.

Also, as shown in FIG. 8, the graph display unit 29 may calculate the average value of blood sugar levels as the processing results for each type of measurement situation information and cause the display 22 to display the average values together with the time series transitive graph of blood sugar levels.

It is also possible that processing results obtained by execution of measurement by the special mode processing unit 36 are stored in the storage unit 25 and the graph display unit 29 causes the display 22 to display a time series transitive graph of the processing results based on the stored content.

Figure 9:
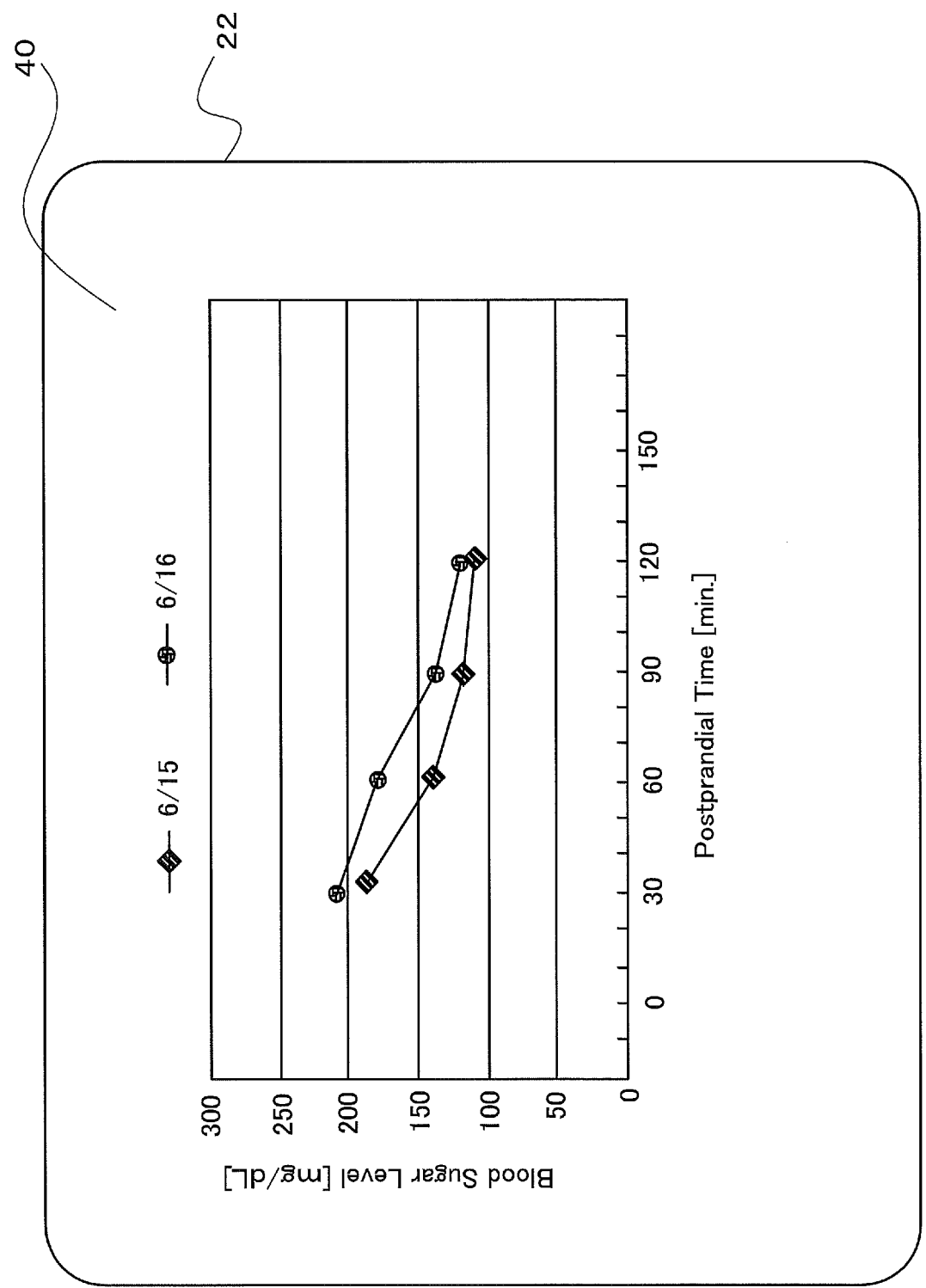
FIG. 9 shows an example of a screen showing transitive graphs indicating measured values and the postprandial time, displayed on the display of the measuring apparatus shown in FIG. 1.

FIG. 9 shows a screen 40 showing transitive graphs indicating measured values and the postprandial time, displayed on the display 22 by the graph display unit 29. As shown in FIG. 9, for example, in the case where the measurement mode has been set to the postprandial-time-based measurement mode, the graph display unit 29 may cause the display 22 to display a time series transitive graph showing changes in blood sugar levels according to postprandial time as the processing results that were obtained by execution of measurement a plurality of times by the special mode processing unit 36, based on the content stored in the storage unit 25. At this time, as shown in FIG. 9, the graph display unit 29 may cause the display 22 to display a time series transitive graph showing the processing results of measurement after meal performed on this occasion so as to be capable of comparison with the time series transitive graph of the processing results of measurement after meal performed previously (for example, the previous occasion). In the case where the measurement mode has been set to the glucose tolerance test measurement mode as well, the graph display unit 29 may cause the display 22 to display a time series transitive graph showing changes in blood sugar levels according to the glucose tolerance test time as processing results that were obtained by execution of measurement a plurality of times by the special mode processing unit 36.

[Operation of Measuring Apparatus]

Figure 10:
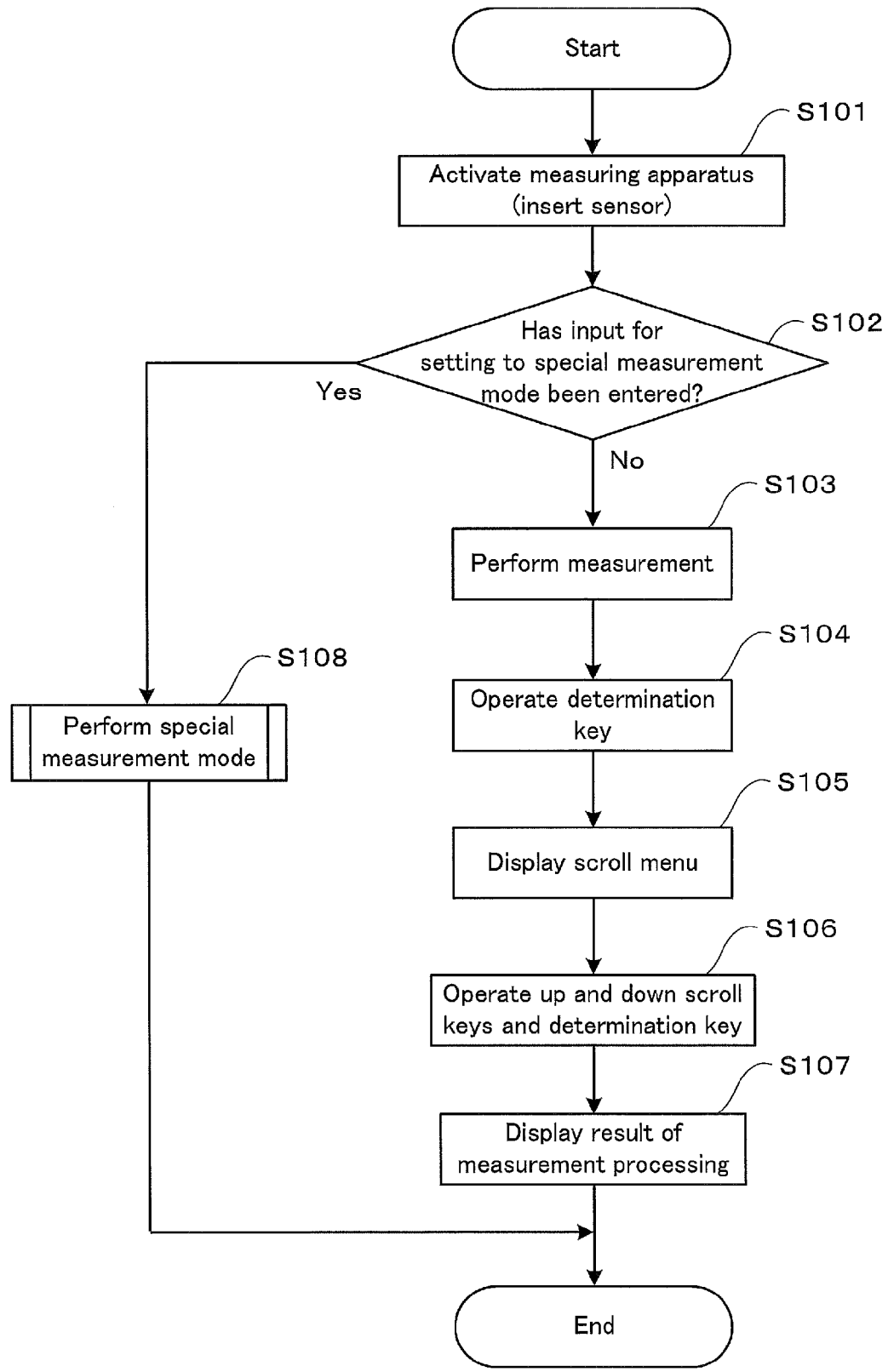
FIG. 10 is a flowchart illustrating an operation of the measuring apparatus shown in FIG. 1.
Figure 11:
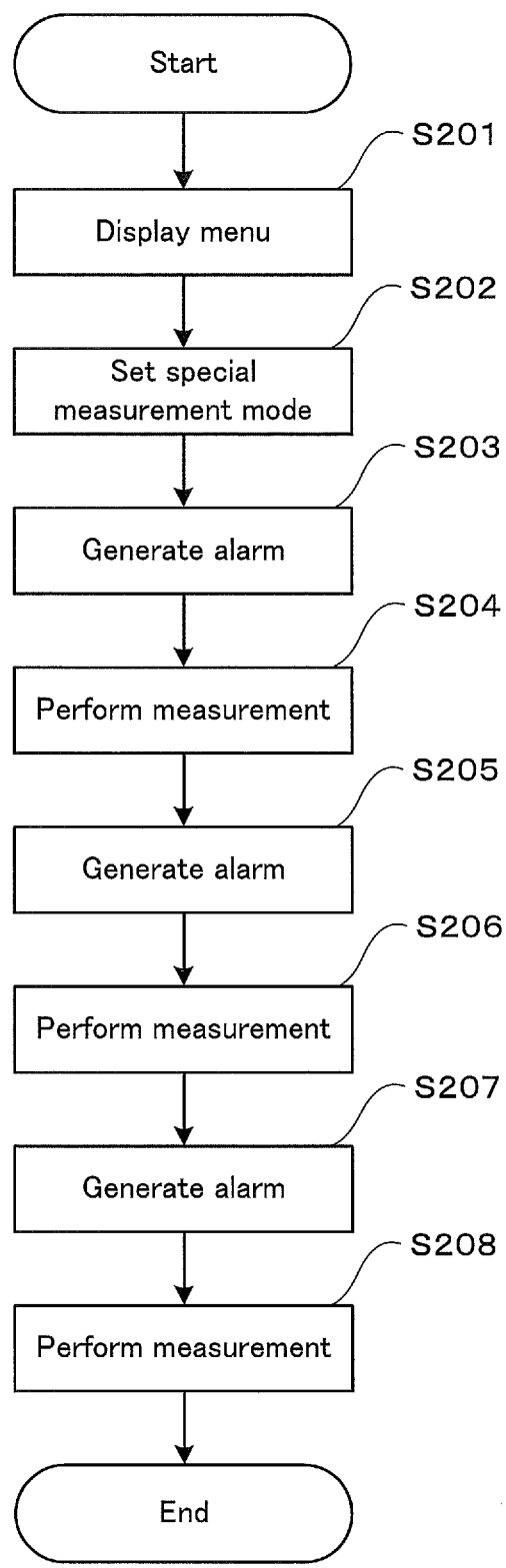
FIG. 11 is a flowchart illustrating an operation performed when the measurement mode has been set to a special measurement mode in the flowchart shown in FIG. 10.
Figure 12:
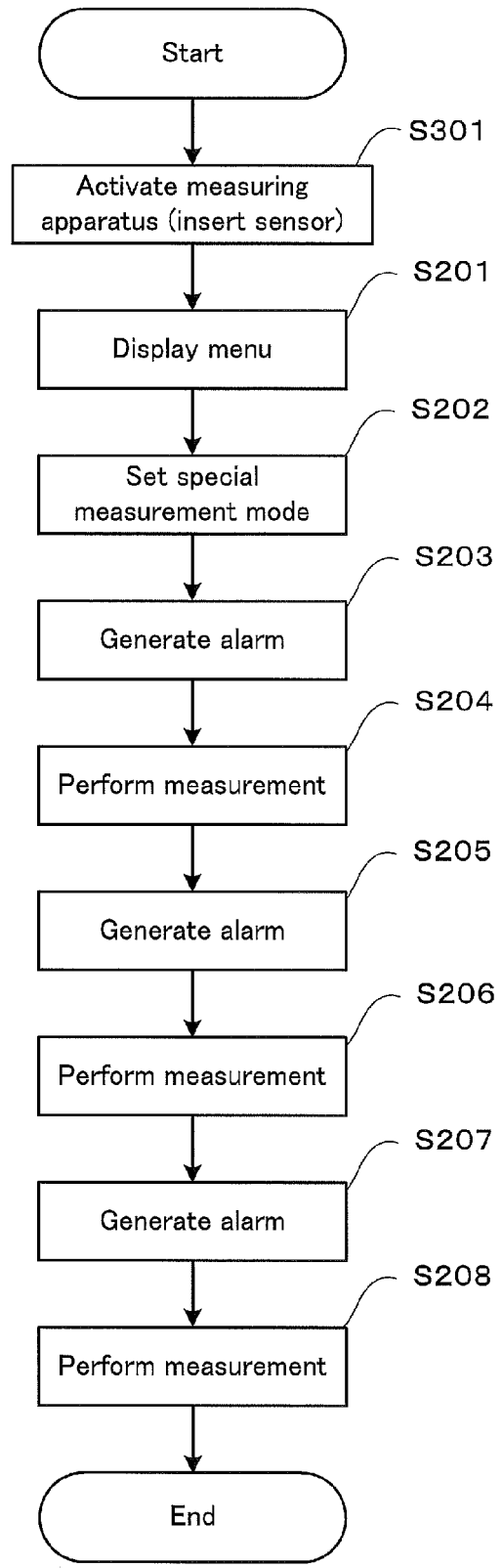
FIG. 12 is a flowchart illustrating a different operation from that of FIG. 10 performed in the measuring apparatus shown in FIG. 1.

Operations of the measuring apparatus 1 according to the embodiment of the present invention will be described next with reference to FIGS. 10 to 12. FIG. 10 is a flowchart illustrating an example of an operation of the measuring apparatus 1 of the present embodiment. FIG. 11 is a flowchart illustrating an example of an operation performed when the measurement mode has been set to a special measurement mode in the flowchart shown in FIG. 10. FIG. 12 is a flowchart illustrating an example of a different operation from that of FIG. 10 performed in the measuring apparatus 1. The following description will be given with appropriate reference to FIGS. 1 to 9.

As shown in FIG. 10, first, when the sensor 10 is inserted into the insertion port 21, the measuring apparatus 1 is thereby activated (step S101). Specifically, a power switch of the measuring apparatus 1 is disposed at the rear of the insertion port 21. The power switch is turned on by insertion of the sensor 10.

Next, the mode determination processing unit 24 determines whether input for setting the measurement mode to a special measurement mode has been entered (step S102). In this case, for example, the mode determination processing unit 24 determines whether a predetermined operation, or in other words, an operation for displaying the menu screen 34 on the display 22 to set the measurement mode to a special measurement mode has been performed by the user before a predetermined period of time passes after the start of activation of the limit switch 33. At this time, if the predetermined operation is not performed before a predetermined period of time passes after the start of activation of the limit switch 33, the mode determination processing unit 24 determines that input for setting the measurement mode to a special measurement mode was not entered.

If it is determined in step S102 that input for setting the measurement mode to a special measurement mode was not entered, then it is determined that the measurement mode has been set to the normal measurement mode. Accordingly, processing is performed based on an instruction from the normal mode processing unit 35, in which measurement was performed on the sample contained in the sensor 10 by the measurement processing unit 26 and the blood sugar level is calculated (step S103). Then, the determination key 23a is press-operated by the user as an operation for performing measurement on the sample contained in the sensor 10 (step S104). With this operation, as described above, the display unit 37 determines the measurement operation timing and causes the display 22 to display a scroll menu screen 38 such that the measurement situation information corresponding to the measurement operation timing is distinguished from other measurement situation information (step S105).

When the scroll menu screen 38 has been displayed on the display 22 in step S105, as described above, the user operates the determination key 23a, or the up and down scroll keys (23b, 23c) and the determination key 23a (step S106). Then, as shown in FIG. 3, a screen showing the result of measurement processing is displayed on the display 22 (step S107). In the screen showing the result of measurement processing, information such as the date and time of the measurement operation timing, the measurement situation information decided by the deciding unit 27, and the result (blood sugar level in the present embodiment) of processing obtained through measurement performed by the measurement processing unit 26 are shown. The measurement when the measurement mode has been set to the normal measurement mode ends here.

If, on the other hand, it is determined in step S102 that the predetermined operation was performed by the user before a predetermined period of time passes after the start of activation of the limit switch 33, the mode determination processing unit 24 determines that input for setting the measurement mode to a special measurement mode has been entered. In this case, in the measuring apparatus 1, an operation when the measurement mode has been set to a special measurement mode is performed. (step 108). FIG. 11 is a flowchart illustrating an example of an operation executed in step S108.

Upon start of the operation shown in FIG. 11, as described above, a menu screen 34 is displayed on the display 22 (step S201). Then, the user operates the up and down scroll keys (23b, 23c) and the determination key 23a and sets the postprandial-time-based measurement mode or the glucose tolerance test measurement mode as the special measurement mode (step S202). At the timing at which either of the special measurement modes is set, the meal start time or the glucose tolerance test start time is stored in the storage unit 25.

When the measurement mode has been set to either of the special measurement modes, namely, either the postprandial-time-based measurement mode or the glucose tolerance test measurement mode (step S202), and a first preset alarm time passes after the timing at which the special measurement mode was set, the alarm unit 30 generates a first alarm to the outside (step S203). When the user connects the sensor 10 to the sensor connection portion 32 in response to the alarm, measurement is executed on the sample contained in the sensor 10 by the measurement processing unit 26 (step S204).

When a second preset alarm time passes after the timing at which the special measurement mode was set, the alarm unit 30 generates a second alarm to the outside (step S205). When the user connects the sensor 10 to the sensor connection portion 32 in response to the alarm, measurement is executed on the sample contained in the sensor 10 by the measurement processing unit 26 (step S206). The second alarm time is set to be longer than the first alarm time.

When a third preset alarm time passes after the timing at which the special measurement mode was set, the alarm unit 30 generates a third alarm to the outside (step S207). When the user connects the sensor 10 to the sensor connection portion 32 in response to the alarm, measurement is executed on the sample contained in the sensor 10 by the measurement processing unit 26 (step S208). The third alarm time is set to be longer than the second alarm time. In the present embodiment, the operation shown in FIG. 11 ends when the third measurement (step S208) has finished. The procedure returns to the operation flow shown in FIG. 10, and the measurement when the measurement mode has been set to a special measurement mode ends. The number of alarms may be two, or may be four or more.

The operation flow shown in FIGS. 10 and 11 was described taking, as an example, the case where the sensor 10 is first inserted into the insertion port 21 to activate the measuring apparatus 1. If the determination key 23a is press-operated first without insertion of the sensor 10, an operation flow shown in FIG. 12 is performed. In this case, the determination key 23a is first press-operated, and the measuring apparatus 1 is thereby activated (step S301). In other words, the measuring apparatus 1 is configured such that its power switch is turned on even when the determination key 23a is operated without the sensor 10 being inserted.

In the case where the determination key 23a is first operated and the measuring apparatus 1 is thereby activated, measurement is performed in the special measurement mode, rather than the normal measurement mode. After activation, the same operation flow as that shown in FIG. 11 is executed. Specifically, steps from step S201 to step S208 are executed.

As described above, in the measuring apparatus 1, based on the time of the timing of measurement operation, a set of measurement situation information corresponding to that measurement operation timing is selected from among a plurality of sets of measurement situation information defined in association with time periods, and displayed in a manner distinguishable from other measurement situation information, and therefore can be identified. The user's operations of operating the operation keys 23 and selecting measurement situation information corresponding to the measurement operation timing can be thereby omitted or eliminated. This eliminates complicated operations that need to be performed repeatedly by the user. Therefore, according to the present embodiment, the user can easily perform the operation for identifying the measurement situation in which measurement was performed.

Also, according to the present embodiment, the user can easily perform the operation for identifying whether the measurement situation in which measurement was performed is before or after each meal (breakfast, lunch and evening meal) or before bedtime. Also, according to the present embodiment, depending on the timing at which before-meal measurement is performed, after-meal measurement situation information can be displayed, and therefore the user's operations can be further simplified flexibly to the user's situation.

Also, according to the present embodiment, the frequencies of time periods of measurement operation timing are determined for each type of measurement situation information based on the past measurement records, and measurement situation information corresponding to the measurement operation timing is displayed on the display 22 according to the determined result. It is therefore possible to continuously learn patterns of time periods during which the user performs measurement, and further simplify the user's operations flexibly to the trends of time periods.

Also, according to the present embodiment, the user can easily check the results of processing by the measuring apparatus plotted on a time series transitive graph for each type of measurement situation information in a distinguishable manner on the display 22 of the measuring apparatus 1. Furthermore, because the transitions of the processing results over time are displayed for each type of measurement situation information in a distinguishable manner, the user can correctly figure out the relationship between the results of processing by the measuring apparatus 1 and the measurement situation in which measurement was performed.

Also, in the present embodiment, measurement is executed a plurality of times when the user sets the measurement mode of the measuring apparatus 1 to a special measurement mode, and an alarm is generated to the outside each time one of a plurality of preset alarm times passes after the timing at which the special measurement mode was set. This frees the user from the onerous burden of having to measure time on the user's side. Furthermore, because an alarm is automatically generated each time one of a plurality of preset alarm times passes, the user does not need to repeatedly perform the setting operation for executing the alarm function, as a result of which the operations can be simplified. Therefore, according to the present embodiment, it is possible to provide a measuring apparatus 1 that can free the user from the onerous burden of having to measure time on the user's side when multiple instances of measurement need to be performed, and also simplify the operations.

Also, in the present embodiment, postprandial-time-based measurement and glucose tolerance test measurement can be set separately as special measurement modes, so the user can figure out the relationship between the results of processing by the measuring apparatus 1 and the special measurement modes in a more detailed and correct manner.

An embodiment of the present invention has been described above, but the present invention is not limited to the embodiment given above, and various modifications are possible within the scope of the claims. The present invention may be widely applied to measurement targets other than blood, and may be implemented as, for example, a weight scale, a pedometer or the like. In the above embodiment, a configuration was described in which the menu screen displayed by the display unit at the measurement operation timing is presented as a scroll menu screen that scrolls up and down, but the configuration may be different. It may be a scroll menu screen that scrolls right and left or a pull-down menu screen that can be pulled down. Also, various modifications are possible with regard to the configuration of the operation keys.

It is also possible to implement a measuring apparatus including a display unit that selects a set of measurement situation information corresponding to the measurement operation timing based on processing results obtained as a result of execution of measurement by the measurement processing unit, rather than based on the time of the measurement operation timing. In this case, the display unit of the measuring apparatus causes a display to display the measurement situation information selected based on the processing results obtained as a result of execution of measurement by the measurement processing unit in a manner distinguishable from other measurement situation information.

In the case of the measuring apparatus including the display unit, if the measurement target is blood, for example, the measurement situation information corresponding to the measurement operation timing is selected based on the levels of blood sugar as the processing results obtained as a result of execution of measurement by the measurement processing unit. For such processing of selecting measurement situation information, for example, the measurement situation information storage unit of the measuring apparatus may be configured such that the measurement situation information stored in association with time periods is also associated with time period-associated blood sugar level ranges that are preset ranges of blood sugar levels corresponding to the time periods. The display unit then identifies, from among the time period-associated blood sugar level ranges, a time period-associated blood sugar level range in which a blood sugar level as a processing result obtained as a result of execution of measurement by the measurement processing unit falls. Furthermore, the display unit selects measurement situation information corresponding to the identified time period-associated blood sugar level range as the measurement situation information corresponding to the measurement operation timing.

As another configuration of the processing of selecting measurement situation information based on processing results obtained as a result of execution of measurement by the measurement processing unit, selection processing of selecting measurement situation information by comparing the average value of past processing results and the current processing result may be carried out. In this case, for example, in the measuring apparatus, each time measurement processing is executed and measurement situation information is determined, a computation is executed to determine, for each type of measurement situation information, a past average value that is the average value of blood sugar levels that are processing results obtained as a result of execution of measurement processing in the past. Furthermore, the past average value obtained as a result of computation is stored in the processing result storage unit of the measuring apparatus in association with the type of measurement situation information. When a blood sugar level as the current processing result is obtained as a result of execution of measurement by the measurement processing unit, for example, the display unit identifies, from among the past average values stored in association with the types of measurement situation information, the past average value that is the closest to the blood sugar level obtained by the current measurement. Furthermore, the display unit selects measurement situation information corresponding to the identified past average value as the measurement situation information corresponding to the measurement operation timing of the current measurement.

As described above, in the case where the processing of selecting measurement situation information based on processing results obtained as a result of execution of measurement by the measurement processing unit is performed, selection of measurement situation information becomes easy. Accordingly, a possibility may arise that the user might carelessly perform an input operation without checking the details of selection, resulting in determination of inappropriate measurement situation information without the user being aware of the fact.

To address the above situation, a configuration may be implemented in which if a value as a processing result falls outside allowable range values that indicate the range of values allowable in relation to the determined measurement situation information, the measuring apparatus determines that the determined measurement situation information may be inappropriate and alerts the user. Alternatively, a configuration may be possible in which if it is determined that the determined measurement situation information may be inappropriate as described above, the measuring apparatus performs a predetermined indication on the display such that the user can later recognize the possibility that the measurement situation information may be inappropriate. The allowable range values may be set, for example, to fall within a predetermined deviation from the average value of processing results of the same measurement situation information for a predetermined number of days of most recent past (for example, within ±1 standard deviation or within ±2 standard deviation). Alternatively, the allowable range values may be set by a user operation.

Also, if the measuring apparatus determines that the determined measurement situation information may be inappropriate, the measuring apparatus may perform, for example, processing of displaying an alarm message on the display or output an alarm sound in order to alert the user, or may perform processing of prompting the user to again check the measurement situation information. In order to allow the user to later recognize the possibility that the measurement situation information may be inappropriate, the measuring apparatus may, for example, display the result of measuring processing on the display in a manner that predetermined marking is attached to the processing result having the possibility that the determined measurement situation information may be inappropriate.

As described above, according to the present invention, with the measuring apparatus, the user can easily perform the operation for identifying the measurement situation in which measurement was performed. The present invention is useful in the field of measurement. The present invention is not limited to the above-described embodiment, and all modifications, applications and equivalents thereof that fall within the claims, for which modifications and applications would become apparent by reading and understanding the present specification, are intended to be embraced therein.

What is claimed is:

1. A measuring apparatus comprising:
   a measurement situation information storage unit in which a plurality of sets of measurement situation information for identifying a measurement situation in which a predetermined measurement is performed on a measurement target are stored in association with time periods;
   a measurement processing unit that executes measurement on the measurement target;
   a display unit that, at a measurement operation timing at which an operation for performing measurement on the measurement target is executed, selects a set of measurement situation information corresponding to the measurement operation timing from among the plurality of sets of measurement situation information stored in the measurement situation information storage unit based on the time of the measurement operation timing or based on processing results obtained as a result of execution of measurement by the measurement processing unit, and causes a display to display the selected measurement situation information in a manner distinguishable from other measurement situation information;
   an operation unit;
   a deciding unit that decides measurement situation information that is displayed on the display as the measurement situation information finally corresponding to the measurement operation timing, based on an input by an operation of the operation unit;
   a storage unit that stores therein the measurement situation information finally corresponding to the measurement operation timing, which is decided by the deciding unit;
   a measurement information storage unit that stores therein information regarding the time of the measurement operation timing and the measurement situation information decided by the deciding unit each time measurement is executed on the measurement target; and
   a frequency determining unit that determines frequencies of time periods to which the times of the measurement operation timing belong for each type of measurement situation information based on the information stored in the measurement information storage unit,
   wherein the display unit is capable of changing a selection of measurement situation information based on, in addition to the time of the measurement operation timing, the resulting frequencies determined by the frequency determining unit.

2. The measuring apparatus according to claim 1,
   wherein information for identifying a before-meal measurement situation and information for identifying an after-meal measurement situation are stored in the measurement situation information storage unit as the measurement situation information.

3. The measuring apparatus according to claim 2,
   wherein, when the before-meal measurement situation information was decided by the deciding unit as the measurement situation information corresponding to a previous measurement operation timing and a current measurement operation timing falls in a time period corresponding to the before-meal measurement situation information that had already been decided on the same day as the day of the current measurement operation timing, the display unit causes the display to display the after-meal measurement situation information as the measurement situation information.

4. The measuring apparatus according to claim 2,
   wherein at least information for identifying a before-breakfast measurement situation, information for identifying an after-breakfast measurement situation, information for identifying a before-lunch measurement situation, information for identifying an after-lunch measurement situation, information for identifying a before-evening meal measurement situation, and information for identifying an after-evening meal measurement situation are stored in the measurement situation information storage unit as the measurement situation information.

5. The measuring apparatus according to claim 1, further comprising: a sensor connection portion to which a sensor is connected,
   wherein the display unit determines a timing at which the sensor containing a sample as the measurement target was connected to the sensor connection portion as the measurement operation timing.

6. The measuring apparatus according to claim 1,
   wherein the measurement target is blood, and the measurement processing unit performs processing of measuring the blood and calculating a blood sugar level.

7. The measuring apparatus according to claim 1, further comprising:
   a processing result storage unit that stores therein the measurement situation information decided by the deciding unit and a processing result obtained as a result of execution of measurement by the measurement processing unit; and
   a graph display unit that causes the display to display a time series transitive graph showing the processing results for each type of measurement situation information in a distinguishable manner based on the content stored in the processing result storage unit.

8. The measuring apparatus according to claim 1, further comprising:
   a mode determination processing unit that determines whether a measurement mode which has been set based on an external operation is a normal measurement mode or the measurement mode is a special measurement mode, and executes processing based on the determined measurement mode, wherein measurement is performed one time in the normal measurement mode, measurement is performed a plurality of times in the special measurement mode.

9. The measuring apparatus according to claim 1, wherein, after the display of the selected measurement situation information in the manner distinguishable from other measurement situation information, the operation unit is configured to receive a user input and transmit a signal corresponding to the user input that results in changing the display on the display unit from the display of the selected measurement situation information to a display of a user-determined measurement situation information based on the input by the operation of the operation unit.

* * * * *